United States Patent
Davis et al.

(10) Patent No.: US 7,602,484 B2
(45) Date of Patent: *Oct. 13, 2009

(54) METHOD AND APPARATUS FOR PERFORMING LIMITED AREA SPECTRAL ANALYSIS

(75) Inventors: Matthew F. Davis, Brookdale, CA (US); Lei Lian, Santa Clara, CA (US); Yasuhiro Uo, Chiba (JP); Michael D. Willwerth, Campbell, CA (US); Andrei Ivanovich Netchitaliouk, Visaginas (LT)

(73) Assignee: Applied Materials, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/952,748

(22) Filed: Dec. 7, 2007

(65) Prior Publication Data
US 2008/0074658 A1    Mar. 27, 2008

Related U.S. Application Data

(60) Continuation of application No. 11/617,221, filed on Dec. 28, 2006, now Pat. No. 7,330,244, which is a division of application No. 10/744,711, filed on Dec. 23, 2003, now Pat. No. 7,158,221.

(51) Int. Cl.
G01N 21/00 (2006.01)
(52) U.S. Cl. .................... 356/237.5; 356/445
(58) Field of Classification Search .................. 356/72, 356/237.4–237.5, 445
See application file for complete search history.

(56) References Cited

U.S. PATENT DOCUMENTS

| | | | |
|---|---|---|---|
| 5,091,320 A | 2/1992 | Aspnes et al. | |
| 5,213,985 A | 5/1993 | Sandroff et al. | |
| 5,313,044 A | 5/1994 | Massoud et al. | |
| 5,450,205 A | 9/1995 | Sawin et al. | |
| 5,793,042 A | 8/1998 | Quick | |
| 5,963,315 A | 10/1999 | Hiatt et al. | |
| 6,038,525 A * | 3/2000 | Maguire et al. | 702/172 |
| 6,348,126 B1 | 2/2002 | Hanawa et al. | |
| 6,410,449 B1 | 6/2002 | Hanawa et al. | |
| 6,449,038 B1 | 9/2002 | Stolze | |
| 6,509,960 B2 | 1/2003 | Johnson et al. | |
| 6,528,751 B1 | 3/2003 | Hoffman et al. | |
| 6,657,736 B1 | 12/2003 | Finarov et al. | |

(Continued)

FOREIGN PATENT DOCUMENTS

RU    2036418    5/1995

(Continued)

OTHER PUBLICATIONS

PCT International Search Report, mail date Jul. 4, 2005, for PCT International Application No. PCT/US2004/043444.

Primary Examiner—Kara E Geisel
(74) Attorney, Agent, or Firm—Moser IP Law Group (57) ABSTRACT

A method and apparatus for obtaining in-situ data of a substrate in a semiconductor substrate processing chamber is provided. The apparatus includes an optics assembly for acquiring data regarding a substrate and an actuator assembly adapted to laterally move the optics assembly in two dimensions relative to the substrate.

20 Claims, 6 Drawing Sheets

U.S. PATENT DOCUMENTS 6,771,374 B1 8/2004 Rangarajan et al.
7,169,254 B2 * 1/2007 Masuda et al. ......... 156/345.24
7,330,244 B2 * 2/2008 Davis et al. .................... 356/72
2002/0054290 A1 5/2002 Vurens et al.
2003/0047449 A1 3/2003 Hanawa et al.

FOREIGN PATENT DOCUMENTS

WO 03041123 A2 5/2003

* cited by examiner

METHOD AND APPARATUS FOR PERFORMING LIMITED AREA SPECTRAL ANALYSIS

CROSS-REFERENCE TO RELATED APPLICATIONS

This application is a continuation of U.S. patent application Ser. No. 11/617,221, filed Dec. 28, 2006 now U.S. Pat. No. 7,330,244, which is a divisional of U.S. patent application Ser. No. 10/744,711, filed Dec. 23, 2003 now U.S. Pat. No. 7,158,221, which are herein incorporated by reference in their entirety.

BACKGROUND OF THE INVENTION

1. Field of the Invention

The present invention generally relates to semiconductor substrate processing. More specifically, the present invention relates to a method and apparatus for performing limited area spectral analysis to monitor a semiconductor substrate process.

2. Description of the Related Art

Integrated circuits have evolved into complex devices that can include millions of components (e.g., transistors, capacitors, resistors, and the like) on a single chip. The evolution of chip designs continually requires faster circuitry and greater circuit density. The demands for greater circuit density necessitate a reduction in the dimensions of the integrated circuit components. The minimal dimensions of features of such devices are commonly referred to in the art as critical dimensions. The critical dimensions generally include the minimal widths of the features, such as lines, columns, openings, spaces between the lines, and the like.

As these critical dimensions shrink, accurate measurement and process control becomes more difficult. For example, one problem associated with a conventional plasma etch process used in the manufacture of integrated circuits is the lack of an ability to accurately monitor the formation of small features on the substrate and thereby accurately monitoring or predicting the endpoint for the etch process. This deficiency leads to lower yields and higher costs of manufacturing such devices.

Therefore, there is a need in the art for an improved method and apparatus for substrate monitoring and process control during the manufacture of integrated circuits.

SUMMARY OF THE INVENTION

The present invention is a method and apparatus for controlling a semiconductor substrate fabrication process including an apparatus for obtaining in-situ data of a substrate in a semiconductor substrate processing chamber. The apparatus includes an optics assembly for acquiring data regarding a substrate and an actuator assembly adapted to laterally move the optics assembly in two dimensions relative to the substrate. The focusing capability of the optics assembly coupled with its movement enable the invention to be used for limited area spectral analysis.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures. It is to be noted, however, that the appended drawings illustrate only exemplary embodiments of this invention and are therefore not to be considered limiting of its scope, for the invention may admit to other equally effective embodiments.

DETAILED DESCRIPTION

The present invention is a method and apparatus for performing limited area spectral analysis to monitor a process for fabricating integrated circuit devices on semiconductor substrates (e.g., silicon substrates, silicon on insulator (SOI) substrates, and the like). The method may provide process control by utilizing substrate state information derived from a reflectance signal collected at a small, designated area of a substrate under process. The method uses the results of pre-etch, during etch, and post-etch measurements of structures being formed on the substrate (i.e., substrate state information) to adjust process recipes and control the operational status of substrate processing equipment. For example, the method may be used to make improved endpoint determinations during an etch process. The measurements are performed in-situ using a dynamic optical measuring tool capable of taking measurements at various small, designated locations on a substrate. The specific location on a product die that is used for measurements can be changed automatically from process step to process step, substrate to substrate, lot to lot, product to product, and the like. The location can be a designated measurement site accessed by movement of the measurement device to preprogrammed positions, or a predetermined location on a product die found by means of scanning and pattern recognition of the monitored reflectance signal. The apparatus is adapted to reliably detect reflectance endpoint conditions of very small substrate structures, such as cache (or embedded) memory arrays which occupy only a small fraction of the total area of a product die on a semiconductor substrate.

Figure 1:
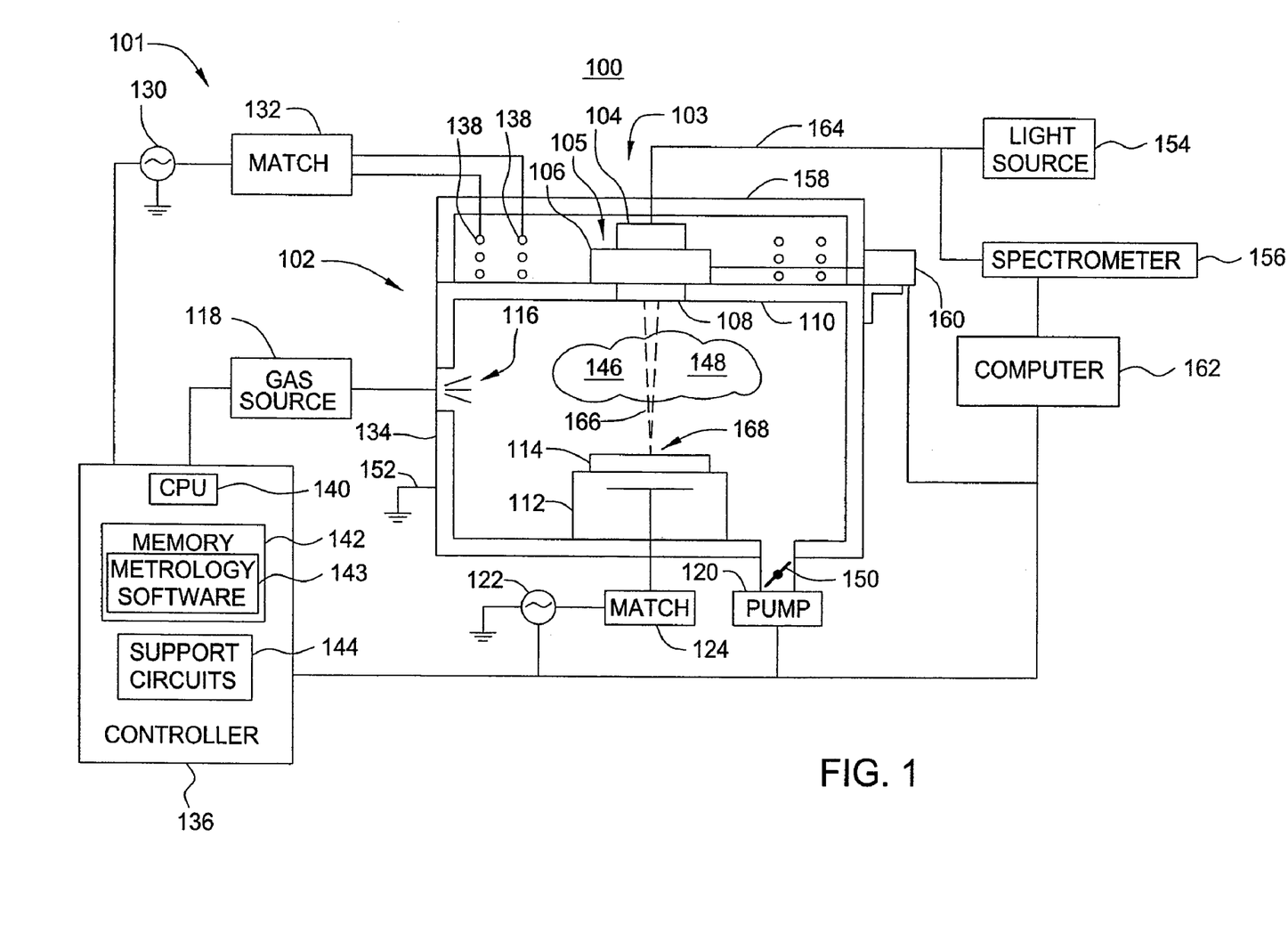
FIG. 1 depicts an exemplary schematic diagram of a processing system having one embodiment of the present invention.

FIG. 1 depicts a schematic diagram of one illustrative embodiment of a semiconductor processing system 100 for fabricating integrated devices suitable for use with the present invention. The system 100 generally includes a plasma processing chamber, such as an etch reactor module 101 having a dynamic in-situ optical measuring tool 103. One illustrative embodiment of an etch reactor module 101 that can be used to perform the steps of the present invention is a Decoupled Plasma Source (DPS®) II etch reactor, available from Applied Materials, Inc. of Santa Clara, Calif. The DPS® II reactor is generally used as a processing module of a larger processing system such as the TRANSFORMA™ system or a CENTURA® system, both of which are available from Applied Materials, of Santa Clara, Calif.

In one embodiment, the reactor module 101 comprises a process chamber 102, a plasma power source 130, a biasing power source 122, and a controller 136. The process chamber 102 comprises a substrate support pedestal 112 within a body (wall) 134, which may be made of a conductive material. The chamber 102 is supplied with a dielectric ceiling 110. In the depicted embodiment, the ceiling 110 is substantially flat. Other embodiments of the chamber 102 may have other types of ceilings, e.g., a curved or domed ceiling. A lid 158 may be additionally provided to house and protect additional components of the reactor 101 as well as form a shield for RF radiation. Above the ceiling 110 and within the lid 158 is disposed an antenna comprising at least one inductive coil element 138 (shown in FIG. 1 as two coil elements 138). The inductive coil element 138 is coupled through a first matching network 132 to the plasma power source 130. The plasma source 130 typically is capable of producing a power signal at a fixed or tunable frequency in a range of from about 50 kHz to about 13.56 MHz.

The support pedestal (cathode) 112 is coupled through a second matching network 124 to the biasing power source 122. The biasing source 122 generally is a source of a power signal at a fixed or tunable frequency of approximately 50 kHz to about 13.56 MHz that is capable of producing either continuous or pulsed power. In other embodiments, the source 122 may be a DC or pulsed DC source.

The controller 136 includes a central processing unit (CPU) 140, a memory 142, and support circuits 144 for the CPU 140 and facilitates control of the components of the DPS II etch process chamber 102 and, as such, of the etch process, as discussed below in further detail. The controller 136 may be one of any form of general-purpose computer processor that can be used in an industrial setting for controlling various chambers and sub-processors. The memory, or computer-readable medium, 142 of the CPU 140 may be one or more of readily available memory such as random access memory (RAM), read only memory (ROM), floppy disk, hard disk, or any other form of digital storage, local or remote. The support circuits 144 are coupled to the CPU 140 for supporting the processor in a conventional manner. These circuits include cache, power supplies, clock circuits, input/output circuitry and subsystems, and the like. The inventive method is generally stored in the memory 142 as a software routine (e.g., metrology software 143). The software routine may also be stored and/or executed by a second CPU (not shown) that is remotely located from the hardware being controlled by the CPU 140.

In a basic etch operation, a substrate 114 is placed on the pedestal 112 and process gases are supplied from a gas panel 118 through one or more entry ports 116 and form a gaseous mixture 146. The gaseous mixture 146 is ignited into a plasma 148 in the chamber 102 by applying power from the plasma and bias sources 130 and 122 to the inductive coil element 138 and the cathode 112, respectively. Typically, the chamber wall 134 is coupled to an electrical ground 152 or other grounding provisions are made. The pressure within the interior of the chamber 102 is controlled using a throttle valve 150 and a vacuum pump 120. The temperature of the wall 134 is controlled using liquid-containing conduits (not shown) that run through the wall 134. Those skilled in the art will understand that other forms of etch chambers may be used to practice the invention, including chambers with remote plasma sources, microwave plasma chambers, electron cyclotron resonance (ECR) plasma chambers, capacitively coupled plasma chambers, and the like.

In order to obtain accurate process measurements, the measuring tool 103 may be configured to perform spectral analysis before, during, and/or after an etch operation as described above. The measuring tool 103 is capable of detecting a broad spectrum of reflected light and analyzing all or portions of the reflectance signal using various analyses, such as interferometry or spectrometry, amongst others. The measuring tool 103 generally includes an optics assembly 104 coupled to an actuator assembly 105, a broadband light source 154, a spectrometer 156, and a computer 162. The computer 162 and controller 136 may be one and the same. However, in one embodiment, the controller 136 is used for controlling the measuring tool 103, while the computer 162 is used for data collection and analysis. The actuator assembly 105 generally includes an XY stage assembly 106 and one or more motors 160 adapted to respond to commands from a controller 136 to move the optics assembly 104 to a desired location. It is contemplated that the XY stage assembly 106 may support multiple optics assemblies 104. The optics assembly 104 generally includes passive optical components, such as a lens, mirrors, beam splitters, and the like and is disposed over a window 108 formed in the ceiling 110 of the chamber 102. The window 108 may be fabricated from quartz, sapphire, or other material that is transparent to light produced by the broadband light source 154. The optics assembly 104 guides and focuses light 166 provided by the broadband light source 154 through the window 108 to form a spot of light which illuminates a specific region 168 of the substrate 114 disposed on the pedestal 112 directly below the window. The illuminated region 168 is generally a large enough area to cover the expected feature to be measured plus an allowance for the expected variation within the manufacturing tolerances. The spot of light generally ranges in size from about 0.1 to about 10 square millimeters.

Light reflected from the illuminated region 168 of the substrate 114 is partially collected and guided by the optics assembly 104 to the spectrometer 156. The spectrometer 156 detects a broad spectrum of wavelengths of light, enabling features on the substrate 114 to be observed using a wavelength having a strong reflectance signal or using multiple wavelengths, thus improving the sensitivity and accuracy of the measuring tool 103. It is contemplated that, more generally, any analyzer capable of analyzing the reflected light and providing an output to the computer 162 may be utilized. It is further contemplated that, in another embodiment of the measuring tool 103, the spectrometer 156 may detect light reflected off of the substrate 114 from a source other than light source 154, such as from a heating lamp or other light source.

The broadband light source 154 is generally a source of light having a wavelength spectrum in the range from about 200 to about 800 nm. Such a broadband light source 154 may include, for example, a mercury (Hg), xenon (Xe), or Hg—Xe lamp, a tungsten-halogen lamp, and the like. In one embodiment, the broadband light source 154 is a xenon flash lamp.

In one embodiment, the optical interface between the optics assembly 104, the broadband light source 154, and the spectrometer 156 may be provided using a fiber-optic array 164. The fiber optic array 164 is generally a bundle of optical fibers in which some fibers (source fibers) are connected to the broadband light source 154 and the remaining fibers (detector fibers) are connected to the spectrometer 156. In one embodiment, the fiber optic array 164 has a combined diameter of about 1 millimeter. The focus of the light emanating from the source fibers of the fiber optic array 164 may be unfocused enough to allow the reflected light to be directed to all of the detector fibers connected to the spectrometer 156. As described in detail below with reference to FIG. 3, the focus may be adjusted by varying the position of the end of the fiber optic array 164 either closer to or farther from the optics assembly 104. The size of the fibers may also vary to assist in the collection of the reflected light. For example, the source fibers connected to the broadband light source 154 may have a diameter of about 100 microns and the detector fibers connected to the spectrometer 156 may have a diameter of about 300 microns. In another embodiment, the fiber optic array 164 may include a single source fiber or an array of source fibers coupled to the broadband light source 154 and passing through a beam splitter that directs the reflected light to the spectrometer 156 without the need for separate detector fibers. The focus in this embodiment may be much sharper since no detector fibers are required to direct the reflected light to the spectrometer 156.

Output from the spectrometer 156 is delivered to the computer 162 for analysis, as discussed further below. The computer 162 may be a general purpose computer or a special purpose computer and generally is configured with similar components as used by the controller 136 described above. The output from the computer 162 is delivered to the controller 136 so that process adjustments may be made if necessary. In another embodiment, the computer 162 and controller 136 may be the same device containing all the required software and hardware components necessary to control the process and analyze the spectral information.

The controller 136 provides a signal to the motor 160 to move the XY stage assembly 106 and the optics assembly 104 to enable taking measurements over a larger area of the substrate 114. This ability facilitates ensuring that the desired features are being measured accurately and enables measurement of a reflectance (interferometric) endpoint condition at a site on the substrate that does not contain complex structures that would otherwise obfuscate the accurate determination of such endpoint conditions. Another advantage of the present invention is ability to measure substrate state information in one area of the die and then moving to another measurement site for in-situ monitoring of substrate state information or interferometric endpoint determination during processing. In one embodiment of the invention, the total movement range of the XY stage assembly 106 encompasses at least the dimensions of one full die of the semiconductor substrate being processed, such that all of the positions of the die can be accessed for measurement. In one specific embodiment, the XY stage assembly 106 provides a range of motion in a square area of about 33 millimeters by about 33 millimeters.

Figure 2:
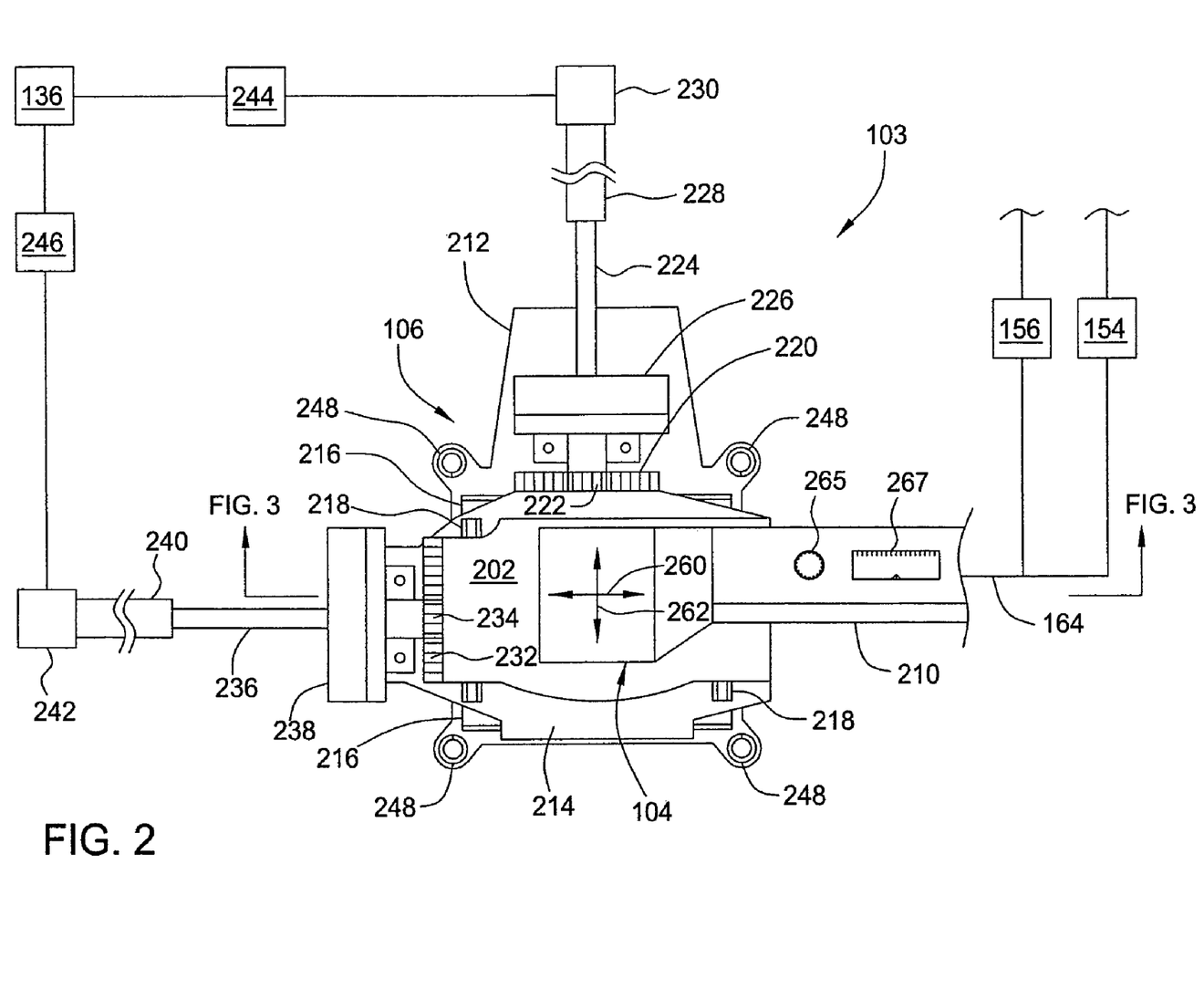
FIG. 2 depicts a plan view of one embodiment of a dynamic in-situ measuring tool of the present invention.
Figure 3:
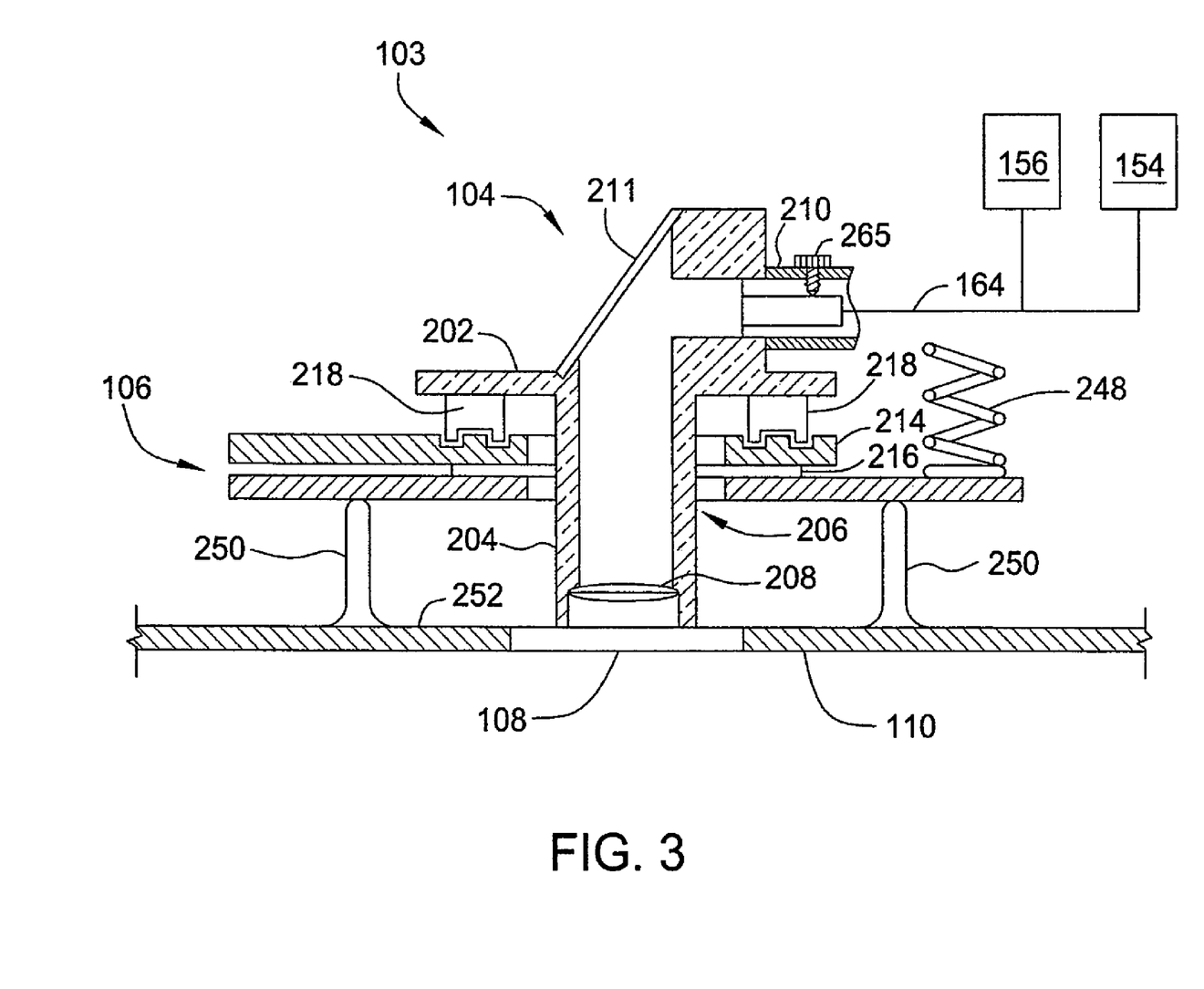
FIG. 3 depicts a side view in partial cross-section of the dynamic in-situ measuring tool of FIG. 2.

FIGS. 2 and 3 respectively depict a plan view and side, cross-sectional view of one embodiment of the optics assembly 104 and the XY stage assembly 106 of the measuring tool 103. In this embodiment, the optics assembly 104 includes a housing 202 coupled to the XY stage assembly 106. The housing 202 has a tubular projection 204 that extends downward through a hole 206 in the XY stage assembly 106 and supports a lens 208 above the window 108 in the ceiling 110 of the process chamber 102. The hole 206 is large enough to allow for movement of the optics assembly 104 in a defined field of motion, as discussed above. The housing 202 is coupled to a conduit 210 that houses and protects the fiber-optic array 164. The array 164 couples the optics assembly 104 to the broadband light source 154 and spectrometer 156. A mirror 211 is positioned in the housing 202 to reflect the light entering the housing 202 from the source fibers in the fiber-optic array 164 downwards through the lens 208 and, conversely, to reflect the light passing upwards through the lens 208 from the chamber 102 to the detector fibers in the fiber-optic array 164.

As referred to above, the focal spot size of the light provided by the light source 154 may be controlled by adjusting the position of the end of the fiber optic array 164 relative to the lens 208. This may be performed by adjusting the position of the conduit 210, or by adjusting the position of the fiber optic array 164 within the conduit. The focus of the light may be manual or automated. For example, in the embodiment depicted in FIGS. 2 and 3, a set screw 265 is disposed within the conduit along with a position indicator 267 for accurate manual setting of the position of the fiber optic array 164 within the conduit 210. Alternatively, control of the focal spot size may be automated. This may be accomplished by, for example, having mating threaded elements (not shown) around the fiber optic array 164 and within the conduit 210 and coupled to a motor drive (not shown) outside of the RF assembly which responds to a manual or automated signal to adjust the position of the fiber optic array 164 within the conduit 210.

The XY stage assembly 106 includes an X stage 212 moveably coupled to a Y stage 214 by a first pair of linear bearings 216. The housing 202 of the optics assembly 104 is moveably coupled to the Y stage 214 by a second pair of linear bearings 218. The first and second pairs of linear bearings 216, 218 are substantially perpendicularly oriented such that movement of the optics assembly 104 by the X and Y stages 212, 214 is substantially orthogonal. A major axis of the XY coordinate system of movement of the XY stage assembly 106 may be aligned with an alignment feature of the substrate 114, such as a notch or flat, such that the XY coordinates of the measured substrate state information from the XY stage assembly correlate to the physical location of the measurement on the substrate 114. In cases where the XY stage assembly 106 is not in alignment with the substrate alignment feature, the XY coordinates from the XY stage assembly 106 can be mathematically transformed, or rotated, to obtain a corresponding XY coordinate of the physical location of the measurement on the substrate 114 relative to the substrate alignment feature.

The XY stage assembly 106 facilitates movement of the optics assembly 104 in a plane substantially parallel to the substrate 114 being measured to prevent misalignment of the optics with the substrate 114. To accomplish this the XY stage assembly 106 must be positioned or mounted substantially parallel to the substrate support pedestal 112. This may generally be accomplished by mounting the XY stage assembly 106 substantially parallel to the ceiling 110 of the chamber 102, which is itself typically substantially parallel with the substrate support pedestal 112. In one embodiment, the XY stage assembly 106 is aligned in a desired orientation when in an operating position. In this embodiment, the XY stage assembly 106 is mounted to the lid 158 of the etch reactor 101 by springs 248 and properly aligns itself when the lid 158 is secured to the ceiling 110 of the chamber 102 by resting on a plurality of projections 250 (e.g., alignment pins) formed on or mounted to an upper surface 252 of the ceiling 110. The springs 248 may be made of a metal having a low magnetic permeability, such as brass, in order to prevent heating due to the RF power proximate the optics assembly during operation.

In one embodiment, a rack gear 220 is disposed on the Y stage 214 substantially parallel with the pair of linear bearings 216 coupling the X and Y stages 212, 214. A pinion gear 222 on the end of a shaft 224 meshes with the rack gear 220 and is held in place by a bearing 226 mounted on the X stage 212. A spline bearing rotating shaft 228 mates with the shaft 224 and is coupled to a stepper motor 230. As the motor 230 rotates, the rack and pinion gears 220, 222 convert the rotary motion to linear motion to move the Y stage 214 along an X axis 260. Similarly, a rack gear 232 is disposed on the housing 202 substantially parallel with the pair of linear bearings 218 coupling the Y stage 214 and housing 202. A pinion gear 234 on the end of a shaft 236 meshes with the rack gear 232 and is held in place by a bearing 238 mounted on the Y stage 214. A spline bearing rotating shaft 240 mates with the shaft 236 and is coupled to a stepper motor 242. As the motor 242 rotates, the rack and pinion gears 232, 234 convert the rotary motion to linear motion to move the housing 202 along a Y axis 262. The spline bearing rotating shafts 228, 240 provide constant contact and support for the shafts 224, 236 throughout the field of motion of the XY stage assembly 106. In addition, flexible couplings, such as 4X flex couplings (not shown), may be used to allow for non-axial movement of the XY stage assembly 106 relative to the shafts 224, 236 and shafts 228, 240.

The stepper motors 230, 242 are respectively controlled through drives 244, 246 by the controller 136. In one embodiment, the stepper motors 230, 242 have an internal rotary encoder and a rotational movement of 0.36 degrees per step. The rack and pinion gears 220, 222 and 232, 234 have a linear positional accuracy of 0.001 inches and convert the rotational motion of the stepper motors 230, 242 into linear motion of 0.1 millimeters per step. In addition, the 4X flex couplings allow for respective misalignment of the shafts 224, 236 and the spline bearing rotating shafts 228, 240 with respect to the XY stage assembly 106. This arrangement allows for precise control of the optics assembly 104 and, therefore, of the measurements taken of the substrate 114.

In one embodiment, the XY stage assembly 106 and optics assembly 104 are designed to fit within the lid 158 and between the RF coils 138 of the etch reactor 101. The stepper motors 230, 242 and drives 244, 246 are maintained outside the RF coils 138 (e.g., outside the lid 158) to avoid interference and damage from the RF environment. The components may be made of a high performance plastic, such as PEEK, that withstands heat as well as the RF frequencies and do not typically impose any non-uniformities in the electromagnetic fields formed in the chamber, and metals having a low magnetic permeability and low eddy current losses within the particular RF environment, such as brass, stainless steel, aluminum, Be—Cu, and like materials, so as to reduce heat generation and electromagnetic field perturbations. In addition, the bearing assemblies 226, 238 are lubricated with a high performance grease that resists ozone attack, such as KRYTOX® available from DuPont, of Wilmington, Del.

The apparatus as described above with reference to FIGS. 1-3 may be utilized to monitor and measure substrate state information as described in U.S. patent application Ser. No. 10/628,001, filed Jul. 25, 2003 by Davis, et al. and U.S. patent application Ser. No. 10/674,568, filed Sep. 29, 2003 by Davis, et al. Further details of how plasma emission spectrum data can be collected and how principal component analysis can be used to identify principal components have been disclosed in commonly assigned U.S. Pat. No. 6,368,975, entitled "Method and Apparatus For Monitoring A Process By Employing Principle Component Analysis", issued on Apr. 9, 2002 and its divisional application Ser. No. 10/341,696, filed on Jan. 14, 2003, U.S. Pat. No. 6,455,437, entitled "Method and Apparatus For Monitoring The Process State of A Semiconductor Device Fabrication Process, issued on Sep. 24, 2002, and U.S. Pat. No. 6,413,867, entitled "Film Thickness Control Using Spectral Interferometry", issued on Jul. 2, 2002. All of the aforementioned patents and applications are hereby incorporated herein by reference in their entireties. Other and further advantages of the present invention are discussed in more detail below.

Figure 4:
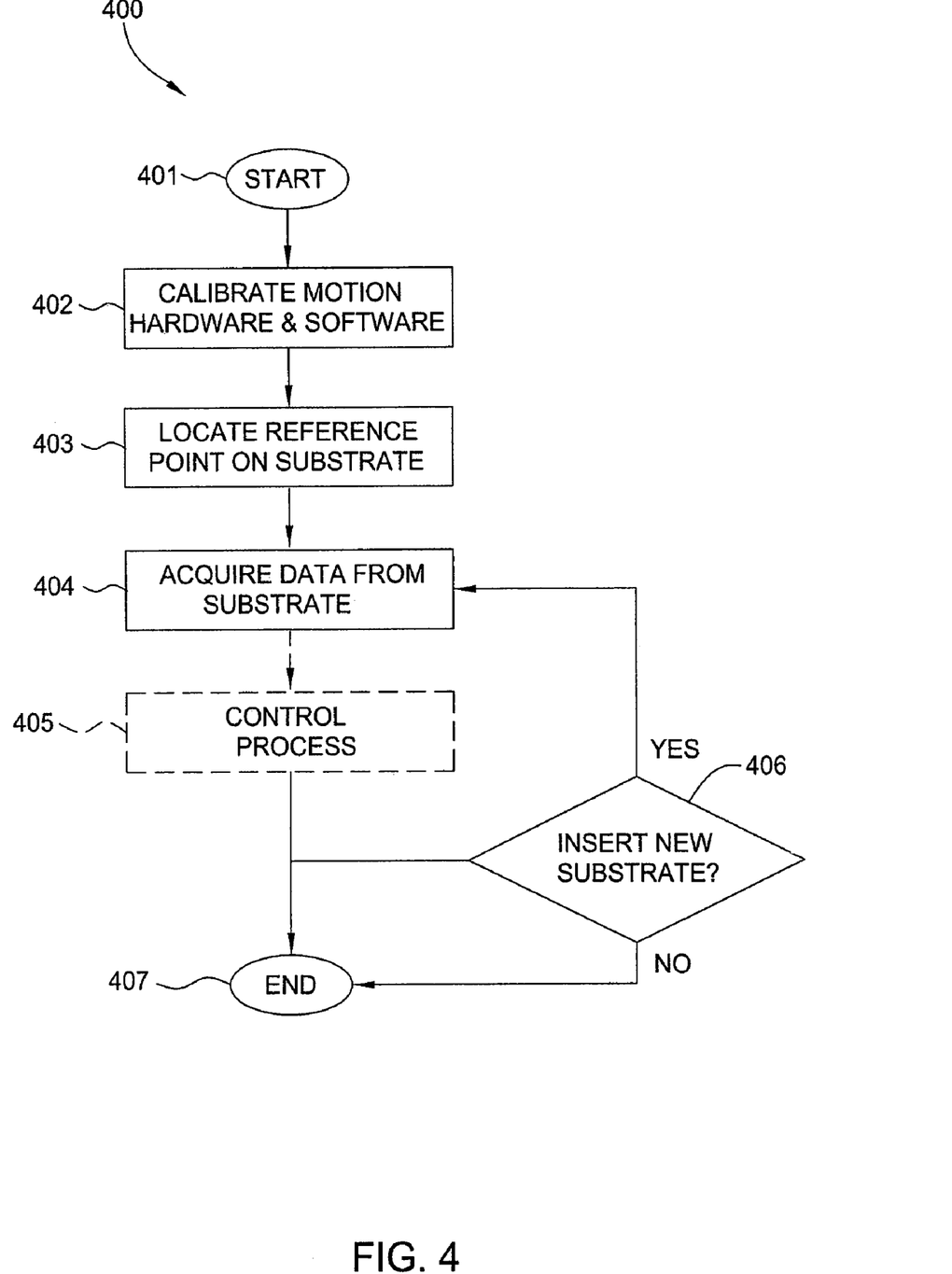
FIG. 4 depicts a flow diagram of a method of monitoring a semiconductor process.

FIG. 4 depicts a flow diagram of one embodiment of the inventive method for monitoring a semiconductor substrate fabrication process. The method 400 is described with reference to FIG. 1. The method 400 begins at step 401 and proceeds to step 402 where the motion hardware and software of the measuring tool 103 is calibrated. The method 400 continues at step 403 where a desired reference point for monitoring the substrate 114 is located. An example of a method for performing this step is described below with reference to FIG. 6. The method 400 continues at step 404 where data is acquired from the substrate 114 using the optics assembly 154 and the spectrometer 156. The data is delivered to the computer 162 for processing. Optionally, the process may be controlled at step 405. In this step, the controller 136 receives the analyzed data from the computer 162 and controls the process in response to the data. The data acquisition step may be repeated throughout a production run as indicated by the decision step 406. The method 400 ends at step 407.

Figure 5:
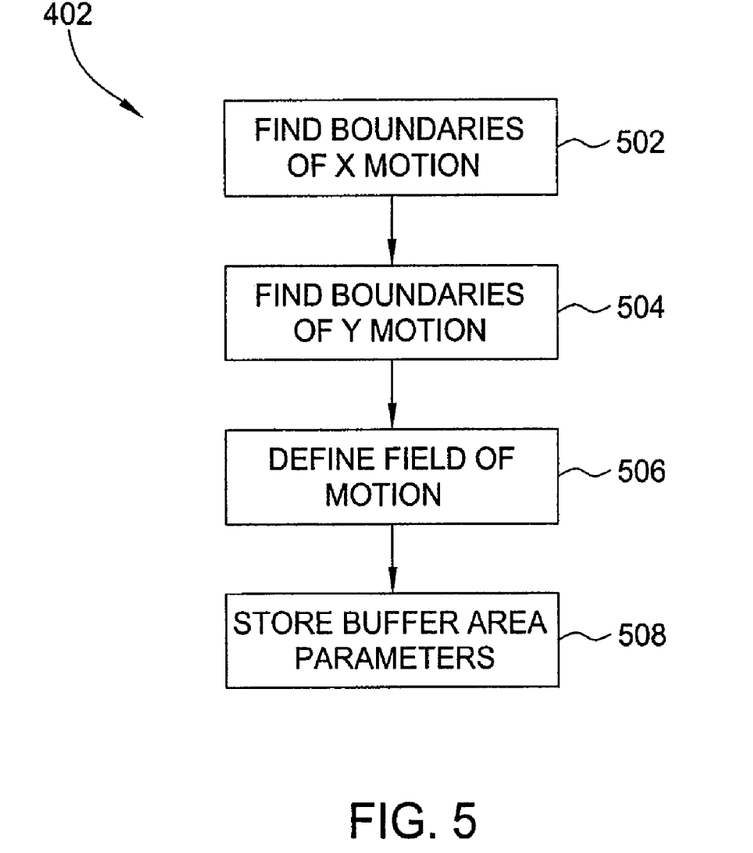
FIG. 5 depicts a flow diagram of one embodiment of a method of calibration of the dynamic in-situ measuring tool.

FIG. 5 depicts a flow diagram of one embodiment of the calibration step 402 of the method 400. This embodiment is described with reference to FIGS. 1-3. In this embodiment, the calibration step 402 begins at step 502, where the boundaries of motion along the X axis 260 are determined. In this step, the controller 136 and the drive 244 direct the motor 230 to move the optics assembly 104 along the X axis 260. The controller 136 monitors the position of the shaft 236, the load on the motor 230, and/or other loading indicia to determine when the extension 204 of the optics assembly 104 comes into contact with an edge of the hole 206 in the XY stage assembly 106 (e.g., the method monitors motor current, torque, shaft positions, and/or other loading indicia). The controller 136 and the drive 244 then direct the motor 230 to move the optics assembly in the opposite direction along the X axis 260 until the controller detects, as described above, that the extension 204 contacts the opposite side of the hole 206.

Next, at step 504, the boundaries of motion along the Y axis 262 are determined in a similar fashion. In this step, the controller 136 and the drive 246 direct the motor 242 to move the optics assembly 104 along the Y axis 262. The controller 136 monitors the position of the shaft 224, the load on the motor 242, and/or other loading indicia to determine when the extension 204 of the optics assembly 104 comes into contact with an edge of the hole 206 in the XY stage assembly 106. The controller 136 and the drive 246 then direct the motor 242 to move the optics assembly in the opposite direction along the Y axis 262 until the controller detects, as described above, that the extension 204 contacts the opposite side of the hole 206.

After determining the boundaries of motion of the XY stage assembly 106 along the X and Y axes 260, 262, the controller defines a constrained field of motion of the XY stage assembly 106 in step 506. In one embodiment, the controller 136 defines a field of motion which is 0.5 millimeters inwards from the edge of the hole 206 in the XY stage assembly 106 (i.e., a buffer area is defined). This embodiment of the calibration method 402 prevents inadvertent jarring of the optics assembly 104 during monitoring and may be performed after the equipment is first powered up, between runs, between lots, or whenever a calibration of the XY stage assembly 106 is desired. At step 508, the method 400 stores the buffer area parameters in memory.

Figure 6:
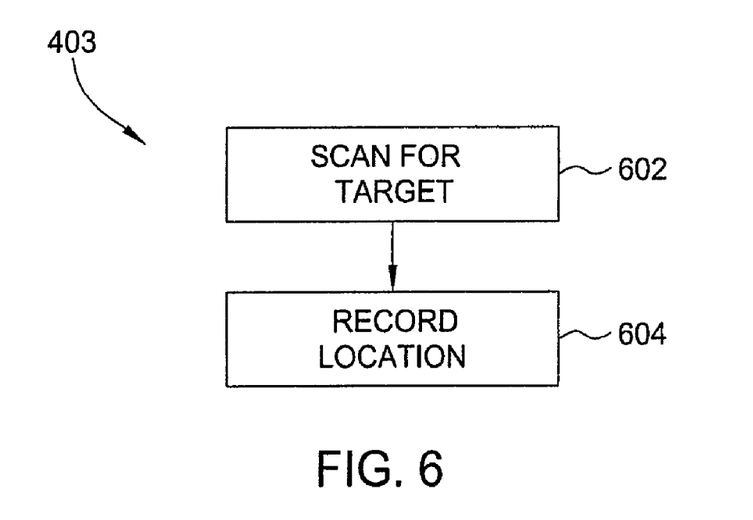
FIG. 6 depicts a flow diagram of one embodiment of a method of positioning the dynamic in-situ measuring tool.

FIG. 6 depicts a flow diagram of one embodiment of the optics positioning step 403 of the method 400. This embodiment is described with reference to FIGS. 1-3. In this embodiment, the optics positioning step 403 begins at step 602, where the controller 136 directs the measuring tool 103 to scan the substrate 114 for the desired target. In one embodiment, the target may be a high-reflectance spot disposed on a substrate designed for calibrating the optics of the measuring tool 103. The high-reflectance spot may be in the center of the substrate 114 or, alternatively, in any desired location on the substrate 114, such as a corresponding location where a desired feature is to be monitored during processing. In another embodiment, the target may include a feature formed on a substrate 114 that has a known "signature" of reflected light such that a feature that is desired to be monitored during processing may be located by comparison of the pattern of reflected light monitored during processing to the calibration signature. It is contemplated that any observable pattern may be utilized as a target for the positioning of the measuring tool 103 and/or monitoring of the substrate 114. For example, in addition to a high-reflectance spot, the target may be a low-reflectance spot, a particular pattern or "signature" on the substrate that is visible in a discrete measurement, a plurality of discrete locations, or over a continuous scan of the substrate 114.

The measuring tool 103 may scan for the target using any known scanning algorithm. In one embodiment, the scan pattern is a spiral pattern where the measuring tool 103 analyzes the reflected light obtained by the spectrometer 156, compares it to a preprogrammed pattern or signal, then either stops if the observed pattern matches the preprogrammed signature of the desired target, or moves the optics assembly 104 to a new location for a new observation and comparison. The measuring tool 103 moves in an outward spiral pattern from the starting point until the desired target is found. The scan may begin from wherever the measuring tool is presently located. Alternatively, the measuring tool may first move to a different starting point, such as an approximate center point of the field of motion or a preprogrammed estimation of the location of the desired target. It is contemplated that any other search algorithm may be utilized to efficiently locate the target on the substrate 114.

Next, at step 604, the location of the target is recorded. In this step the location of the target is recorded by the measuring tool 103 so that the measuring tool may utilize that location as a starting point for monitoring desired features of further substrates being processed. Steps 602, 604 may be repeated on a single or multiple substrates to find multiple targets as well.

Figure 7:
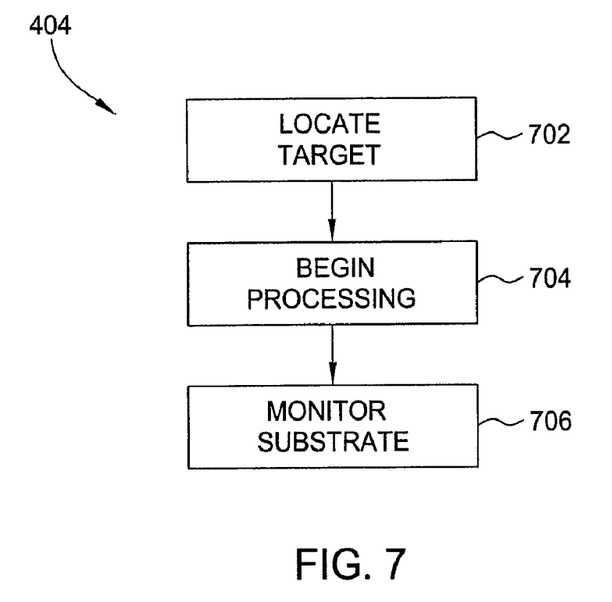
FIG. 7 depicts a flow diagram of one embodiment of a method of obtaining data utilizing the dynamic in-situ measuring tool.

FIG. 7 depicts a flow diagram of one embodiment of the data acquisition step 404 of the method 400. This embodiment is described with reference to FIGS. 1-3. The data acquisition step 404 begins at step 702 where the measuring tool 103 locates the desired target. This step may include moving to a known location obtained from a previous calibration step, such as described above with reference to FIG. 6, or from a previous data acquisition step, such as from a previous run or lot. Alternatively, step 702 may include scanning the substrate 114 to find the desired location by comparison of the reflectance signal obtained from the substrate 114 being monitored to a known reflectance signature stored in the computer 162. This scan for the desired location enables the measuring tool to accurately measure the desired feature. For example, misalignment of the substrate 114 or variation between substrates may be compensated for by the ability of the measurement tool 103 to scan the substrate 114 for the desired feature to be monitored.

Next, at step 704, processing of the substrate 114 begins. The processing may be an etch process as described above with reference to FIG. 1. Other applications may include, but are not limited to photomask etch to determine key feature phase shift depths in-situ using the scan and measure method, PECVD in-situ evaluation of via fill operations, MOCVD in-situ evaluation of step coverage, or granularity/reflectivity determinations of metal or Cu seed layers.

At step 706, the substrate 114 is monitored by the measuring tool 103. This step may include monitoring of a desired location to determine the endpoint of an etch process. For example, the desired location may be monitored by the measuring tool 103 until the reflectance pattern observed by the measuring tool 103 matches a known reflectance pattern, at which time the controller 136 ends the etch process. Alternatively, if the feature being observed is complex or otherwise yields a weak reflectance signal, an alternate location may be observed that correlates to the target location and has a stronger reflectance signal which may be more easily monitored.

Figure 8:
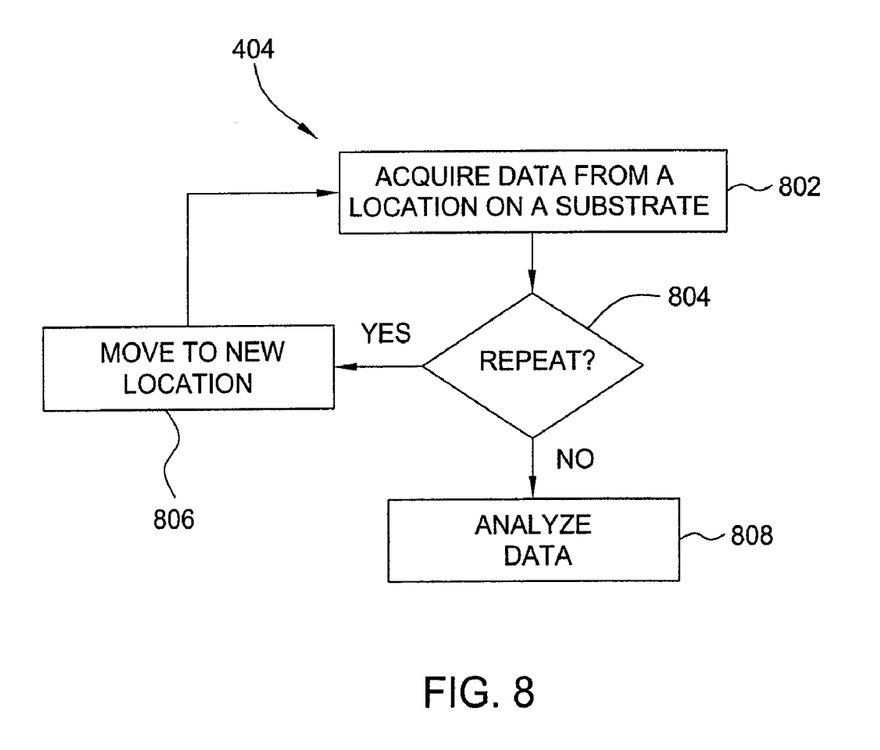
FIG. 8 depicts a flow diagram of another embodiment of obtaining data utilizing the dynamic in-situ measuring tool.

FIG. 8 depicts a flow diagram of another embodiment of the data acquisition step 404 of the method 400. This embodiment is described with reference to FIGS. 1-3. The step 404 begins at step 802 where the measuring tool 103 acquires data from the substrate 114 at a given location. Next, at step 804, a decision is made to either acquire more data from a new location on the substrate 114 or to analyze the data already obtained. If more data is desired, the method 404 continues at step 806 where the measuring tool 103 is moved to a new location over the substrate 114. Step 802 is then repeated as data is acquired from the new location over the substrate 114. Step 804 is also repeated, enabling data to be obtained at yet another location over the substrate 114. This cycle may be repeated as desired until it is desired to analyze the acquired data at step 808. The path along which the measuring tool 103 is moved with respect to the substrate 114 may include any known scanning algorithm. Alternatively, the measuring tool 103 may be moved along a predetermined path that corresponds to some feature on the substrate 114 that is desired to be measured, for example, along a trench being formed in the substrate 114. These steps generally provide for scanning the substrate 114 and obtaining reflectance measurements over a range of locations and comparing those measurements to known patterns or signatures to determine the overall quality of the substrate 114. For example, multivariate analysis may be performed on the data and the results compared to that of known good quality substrates to detect faults, misprocessing, geometry variations, uniformity, and the like. It is contemplated that the data obtainment steps 404 described in FIGS. 7 and 8 may be simultaneous performed. For example, while scanning the substrate 114 to find the target location for etch depth monitoring, the data obtained can be analyzed to obtain a database of reflectance measurements at various portions of the substrate being monitored. It is further contemplated that the monitoring of the substrate 114 and acquisition of data therefrom by the measuring tool is not limited to the embodiments described in detail herein and may further include acquiring data from the substrate 114 before, during, or after searching for a target location on the substrate 114 and before, during, and/or after processing of the substrate 114.

Thus, a method and apparatus for process control and substrate state determination has been provided. The invention enables accurate control of etch-to-depth operations on applications which have very low active etch area fractions. The invention also enables the ability to measure substrate state information on one area of a die and monitor or control the endpoint on another area of the substrate by moving the optics from one location to another during processing. The invention also provides the ability to determine the reflectance of a substrate at the optimal location on a die to control etch endpoint more accurately in situations where most of the surface area contains structure that creates complexity in the reflected optical signal. Furthermore, as in situ data is obtainable for every wafer processed using the present invention, metrology/wafer state information is available for each wafer—rather than just for the send-ahead or production monitor wafers typically used in the current state of the art. The in situ aspect of the measurement/metrology methods and apparatus disclosed herein allow for fab-wide process monitoring, or Advanced Process Control (APC). Although the embodiments and examples provided herein discuss the invention with respect to an etch process, it is contemplated that other semiconductor fabrication processes may be monitored and controlled by the teachings disclosed herein.

While the foregoing is directed to the illustrative embodiment of the present invention, other and further embodiments of the invention may be devised without departing from the basic scope thereof, and the scope thereof is determined by the claims that follow.

What is claimed is:

1. A method of monitoring a substrate in a semiconductor substrate processing chamber, comprising:
   acquiring data at a first location on a substrate disposed in a semiconductor substrate processing chamber using an in-situ measuring tool, the measuring tool moveable along two axes;
   moving the measuring tool to at least a second location over the substrate;
   acquiring data at least a second location on the substrate; and
   analyzing the acquired data to identify defects in the monitored substrate.

2. The method of claim 1, wherein analyzing the acquired data further comprises:
   performing multivariate analysis of the acquired data.

3. The method of claim 2, wherein analyzing the acquired data further comprises:
   comparing the multivariate analysis of the monitored substrate to a stored multivariate analysis of a known reference substrate to identify defects in the monitored substrate.

4. The method of claim 1, further comprising:
   controlling the process in response to the acquired data.

5. The method of claim 4, wherein the controlling further comprises:
   determining an endpoint of a process being performed on the substrate.

6. The method of claim 5, further comprising:
   monitoring a desired location with the measuring tool until a reflectance pattern observed by the measuring tool matches a known reflectance pattern.

7. The method of claim 5, further comprising:
   detecting a first reflectance signal at a target location on the substrate; and
   monitoring a second location on the substrate that correlates to the target location to detect a second reflectance signal that is stronger than the first reflectance signal.

8. A method of monitoring a substrate in a semiconductor substrate processing chamber, comprising:
   providing an etch chamber having an in-situ measuring tool, the measuring tool moveable along two axes;
   acquiring data at a first location on a substrate disposed in the etch chamber using the measuring tool;
   moving the measuring tool to at least a second location over the substrate;
   acquiring data at least a second location on the substrate; and
   analyzing the acquired data to identify defects in the monitored substrate.

9. The method of claim 8, further comprising:
   scanning the substrate for a target; and
   recording the location of the target.

10. The method of claim 9, wherein the target is a high-reflectance spot disposed in a desired location on an alignment substrate.

11. The method of claim 9, wherein the target is a feature formed on a substrate.

12. The method of claim 8, wherein the data acquisition step further comprises:
    locating a target on the substrate; and
    monitoring the substrate.

13. The method of claim 12, wherein the substrate is monitored at the target location.

14. The method of claim 12, wherein the substrate is monitored at a predetermined offset from the target location.

15. The method of claim 8, wherein analyzing the acquired data further comprises:
    performing multivariate analysis of the acquired data.

16. The method of claim 12, further comprising:
    controlling the process in response to the acquired data.

17. The method of claim 16, wherein the controlling further comprises:
    determining an endpoint of an etch process being performed on the substrate.

18. The method of claim 12, further comprising:
    monitoring the target location with the measuring tool until a reflectance pattern observed by the measuring tool matches a known reflectance pattern.

19. The method of claim 8, further comprising:
    detecting a first reflectance signal at a target location on the substrate; and
    monitoring a second location on the substrate that correlates to the target location to detect a second reflectance signal that is stronger than the first reflectance signal.

20. A method of monitoring a substrate in a semiconductor substrate processing chamber, comprising:
    acquiring data at a first location on a substrate disposed in a semiconductor substrate processing chamber using an in-situ measuring tool, the measuring tool moveable along two axes;
    moving the measuring tool to at least a second location over the substrate;
    acquiring data at the second location on the substrate;
    detecting a first reflectance signal at a target location on the substrate; and
    monitoring a second location on the substrate that correlates to the target location to detect a second reflectance signal that is stronger than the first reflectance signal.

* * * * *